US012748107B2

(12) United States Patent
Liu et al.

(10) Patent No.: US 12,748,107 B2
(45) Date of Patent: Sep. 29, 2026

(54) IMMUNOASSAY DEVICE AND IMMUNOASSAY METHOD

(71) Applicants: Beijing BOE Technology Development Co., Ltd., Beijing (CN); BOE TECHNOLOGY GROUP CO., LTD., Beijing (CN)

(72) Inventors: Haonan Liu, Beijing (CN); Xiangguo Ma, Beijing (CN); Kai Geng, Beijing (CN); Ding Ding, Beijing (CN)

(73) Assignees: Beijing BOE Technology Development Co., Ltd., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 1251 days.

(21) Appl. No.: 17/639,078

(22) PCT Filed: Apr. 29, 2021

(86) PCT No.: PCT/CN2021/091123

§ 371 (c)(1),
(2) Date: Feb. 28, 2022

(87) PCT Pub. No.: WO2022/226920

PCT Pub. Date: Nov. 3, 2022

(65) Prior Publication Data

US 2024/0036036 A1 Feb. 1, 2024

(51) Int. Cl.

| | |
|---|---|
| ***G01N 33/543*** | (2006.01) |
| ***B01L 3/00*** | (2006.01) |
| ***G01N 35/10*** | (2006.01) |

(52) U.S. Cl.
CPC .. *G01N 33/54306* (2013.01); *B01L 3/502761* (2013.01); *G01N 33/54386* (2013.01);
(Continued)

(58) Field of Classification Search
None
See application file for complete search history.

(56) References Cited

U.S. PATENT DOCUMENTS 6,190,617 B1 * 2/2001 Clark .................... G01N 21/03 422/562
6,440,369 B1 * 8/2002 Oonuma .......... G01N 35/00594 422/63

(Continued)

FOREIGN PATENT DOCUMENTS

CN 102472757 A 5/2012
CN 103399161 A 11/2013

(Continued)

*Primary Examiner* — Rebecca M Giere
(74) *Attorney, Agent, or Firm* — HOUTTEMAN LAW LLC

(57) ABSTRACT

An immunoassay device and an immunoassay method are provided. The immunoassay device includes: a housing, a driving assembly, a detection chip and a liquid storage chamber; the housing has a first accommodating part in which the detection chip is disposed and a second accommodating part in which the liquid storage chamber is disposed, and the liquid storage chamber is configured at least to store reagent; the driving assembly is configured to communicate a liquid outlet of the liquid storage chamber with a liquid inlet of the detection chip, and drive the reagent in the liquid storage chamber to enter the detection chip.

18 Claims, 7 Drawing Sheets

(52) U.S. Cl.
CPC ...... *G01N 35/10* (2013.01); *B01L 2200/0647* (2013.01); *B01L 2200/16* (2013.01); *B01L 2300/027* (2013.01); *B01L 2300/0636* (2013.01)

(56) References Cited

U.S. PATENT DOCUMENTS

| | | | | |
|---|---|---|---|---|
| 2006/0275922 | A1* | 12/2006 | Gould .............. | G01N 33/54389 436/514 |
| 2012/0058465 | A1* | 3/2012 | Mori ................ | G01N 33/54388 435/5 |
| 2012/0107850 | A1 | 5/2012 | Maruyama et al. | |
| 2013/0052331 | A1 | 2/2013 | Kram et al. | |
| 2016/0299165 | A1 | 10/2016 | Zhou | |
| 2017/0095811 | A1 | 4/2017 | Boehm et al. | |
| 2018/0292398 | A1* | 10/2018 | Wada ............... | G01N 33/54388 |

FOREIGN PATENT DOCUMENTS

| | | | |
|---|---|---|---|
| CN | 103954782 | A | 7/2014 |
| CN | 104745452 | A | 7/2015 |
| CN | 104833812 | A | 8/2015 |
| CN | 104870974 | A | 8/2015 |
| CN | 105647789 | A | 6/2016 |
| CN | 106660040 | A | 5/2017 |
| CN | 107976402 | A | 5/2018 |
| CN | 108226547 | A | 6/2018 |
| CN | 110806399 | A | 2/2020 |
| CN | 210474332 | U | 5/2020 |
| CN | 111349545 | A | 6/2020 |
| CN | 111774115 | A | 10/2020 |
| EP | 2762887 | * | 2/2019 |

* cited by examiner

IMMUNOASSAY DEVICE AND IMMUNOASSAY METHOD

TECHNICAL FIELD

The present disclosure belongs to the field of biological detection, and particularly relates to an immunoassay (immunodetection) device and an immunoassay method.

BACKGROUND

The in vitro diagnostic industry is divided into biochemical diagnosis, molecular diagnosis and immunodiagnosis according to principle. In recent years, the immunodiagnosis becomes the largest sub-field of in vitro diagnosis.

SUMMARY

The present disclosure seeks to solve at least one of the technical problems in the existing technology, and provides an immunoassay device and an immunoassay method. In order to achieve the above object, the present disclosure provides an immunoassay device, including: a housing, a driving assembly, a detection chip and a liquid storage chamber. The housing has a first accommodating part and a second accommodating part, and the detection chip is disposed in the first accommodating part, and the liquid storage chamber is disposed in the second accommodating part, and the liquid storage chamber is configured at least to store reagent. The driving assembly is configured to communicate a liquid outlet of the liquid storage chamber with a liquid inlet of the detection chip, and drive the reagent in the liquid storage chamber to enter the detection chip.

In some embodiments, the driving assembly includes: a controller, a driver and a conveyer. The controller is connected to the driver, the driver is connected to the conveyer, and the controller is configured to control the driver to drive the conveyer so that the conveyer controls the reagent to flow.

In some embodiments, the conveyor includes: a flow direction regulating member and a syringe pump. The syringe pump includes: a pump body and a piston rod. A piston end of the piston rod extends into the pump body from a first pump port of the pump body, an actuating end of the piston rod is connected to the driver, and the piston rod moves under control by the driver, so that the syringe pump sucks or discharges the reagent through a second pump port. The flow direction regulating member has a first opening, a second opening and a third opening. The first opening communicates with the second pump port of the syringe pump, the second opening communicates with the liquid inlet of the detection chip, and the third opening communicates with the liquid outlet of the liquid storage chamber. The flow direction regulating member is configured to communicate one of the second opening and the third opening with the first opening under drive by the driver.

In some embodiments, the housing includes: a top wall and a bottom wall disposed opposite to each other, and a side wall connected between the top wall and the bottom wall. The first accommodating part is disposed on a side of the top wall away from the bottom wall, and the second accommodating part is formed on the side wall. The driving assembly is disposed in a space enclosed by the top wall, the bottom wall and the side wall.

In some embodiments, the first accommodating part is a first groove formed on the top wall, the immunoassay device further includes: a cover plate configured to define a darkroom with the first groove.

In some embodiments, the cover plate is hinged to the top wall so as to open or close the darkroom.

In some embodiments, a display is further included, the display being disposed on a side of the top wall close to the bottom wall and configured to display driving parameters of the driving assembly; and a hollowed-out portion is disposed on the top wall and exposes a display area of the display.

In some embodiments, a fixing plate is disposed on the side wall, and the driving assembly comprises a controller fixed to the fixing plate.

In some embodiments, the liquid storage chamber includes: a body part, a first liquid tank and a second liquid tank. The first liquid tank and the second liquid tank are disposed on the body part. The first liquid tank is configured to store the reagent, a liquid outlet of the first liquid tank serves as the liquid outlet of the liquid storage chamber; and a liquid inlet of the second liquid tank communicates with the liquid outlet of the detection chip. The second liquid tank is configured to store waste liquid discharged from the detection chip.

In some embodiments, the body part is provided with a first mounting hole and a second mounting hole, the first liquid tank is inserted into the first mounting hole, and a second mounting hole the second liquid tank is inserted into the first mounting hole.

In some embodiments, a plurality of connecting hose are further included. The liquid inlet of the second liquid tank is connected to the liquid outlet of the detection chip by the connecting hose, and the liquid outlet of the first liquid tank is connected to the driving assembly by the connecting hose. The first liquid tank includes: a first liquid storage tube and a first sealing cover, a liquid outlet of the first liquid tank being disposed on the first sealing cover and communicating with the first liquid storage tube through a flow channel in the first sealing cover. The second liquid tank includes: a second liquid storage tube and a second sealing cover, a liquid inlet of the second liquid tank being disposed on the second sealing cover and communicating with the second liquid storage tube through a flow channel in the second sealing cover.

In some embodiments, at least one of the first liquid storage tube and the second liquid storage tube includes a centrifuge tube.

In some embodiments, a first guide portion is disposed on an inner wall of the second accommodating part, a second guide portion which cooperates with the first guide portion is disposed on the body part, and the second guide portion is configured to move along the first guide portion so as to move the liquid storage chamber into or out of the second accommodating part.

In some embodiments, a chip clamp is further included, the chip clamp being disposed in the first accommodating part and configured to clamp the detection chip.

In some embodiments, the chip clamp includes: a first clamping portion and a second clamping portion hinged to each other. A second groove is disposed on a side of the first clamping portion facing the second clamping portion, and the second groove is configured to accommodate the detection chip. The second clamping portion is provided with a first open hole and a second open hole, the first sealing member is disposed in the first open hole, and a second sealing member is disposed in the second open hole, the first sealing member having a first through hole, and the second sealing member having a second through hole. The first through hole has a first bottom end opening close to the detection chip and a first top end opening away from the detection chip, the first top end opening communicating with the driving assembly. The second through hole has a second bottom end opening close to the detection chip and a second top end opening away from the detection chip. When the chip clamp is in a clamping state, the first sealing member and the second sealing member are both in close contact with the detection chip, and an orthographic projection of the first bottom end opening of the first through hole on the detection chip overlaps with an area where the liquid inlet of the detection chip is located; and an orthographic projection of the second bottom end opening of the second through hole on the detection chip overlaps with an area where the liquid outlet of the detection chip is located.

In some embodiments, when the chip clamp is in the clamping state, the area where the liquid inlet of the detection chip is located is within an orthographic projection range of the first bottom end opening on the detection chip; the area where the liquid outlet of the detection chip is located is within an orthographic projection range of the second bottom end opening on the detection chip.

In some embodiments, the first sealing member and the second sealing member are each an elastic member, and the first sealing member and the second sealing member are each in a compressed state when the chip clamp is in the clamping state.

In some embodiments, the liquid storage chamber includes: a first liquid tank and a second liquid tank. The first liquid tank is configured to store the reagent, a liquid outlet of the first liquid tank serves as the liquid outlet of the liquid storage chamber. The second liquid tank is configured to store waste liquid discharged from the detection chip.

A liquid inlet of the second liquid tank communicates with the second top end opening of the second through hole.

In some embodiments, a connecting member is disposed at an end of the first clamping portion away from a hinged position; and an engaging member is disposed at an end of the second clamping portion away from the hinged position. When the chip clamp is in the clamping state, the connecting member is engaged with the engaging member.

In some embodiments, the housing has a length between 25 cm and 40 cm, a width between 20 cm and 30 cm, and a height between 15 cm and 25 cm; a dimension of the detection chip is between 70 mm and 80 mm in length, between 20 cm and 30 cm in width, and between 1.0 mm and 2.0 mm in thickness.

The embodiment of the present disclosure further provides an immunoassay method for an immunoassay device as described above, and the immunoassay method includes:

- adding a sample solution with antigen into the detection chip to combine at least a part of the antigen in the sample solution with a fluorescent antibody preset in the detection chip, and a complex formed after combination being captured by a capture object preset in the detection chip; and
- utilizing the driving assembly to drive the liquid outlet of the liquid storage chamber to communicate with the liquid inlet of the detection chip, and drive the reagent in the liquid storage chamber to enter the detection chip, so as to wash away the fluorescent antibody that is not combined with the antigen.

BRIEF DESCRIPTION OF DRAWINGS

The accompanying drawings, which are included to provide a further understanding of the disclosure and constitute a part of this specification, serve to explain the disclosure together with the embodiments described hereinafter, but do not constitute a limitation of the disclosure.

DETAIL DESCRIPTION OF EMBODIMENTS

The embodiments of the present disclosure are described in further detail below with reference to the accompanying drawings. It should be understood that the embodiments described herein below are merely used to describe and explain the present disclosure only and are not intended to limit the present disclosure.

The development of immunoassay has two main trends, one is a product that is miniaturized, simple and convenient to use and quick qualitative, which has the defects of low sensitivity and impossible quantification; the other is a product that is a large-scale, high-sensitivity, high-flux and quantitative, which has the defects of larger volume, complex operation, low detection speed and no portability.

Figure 1:
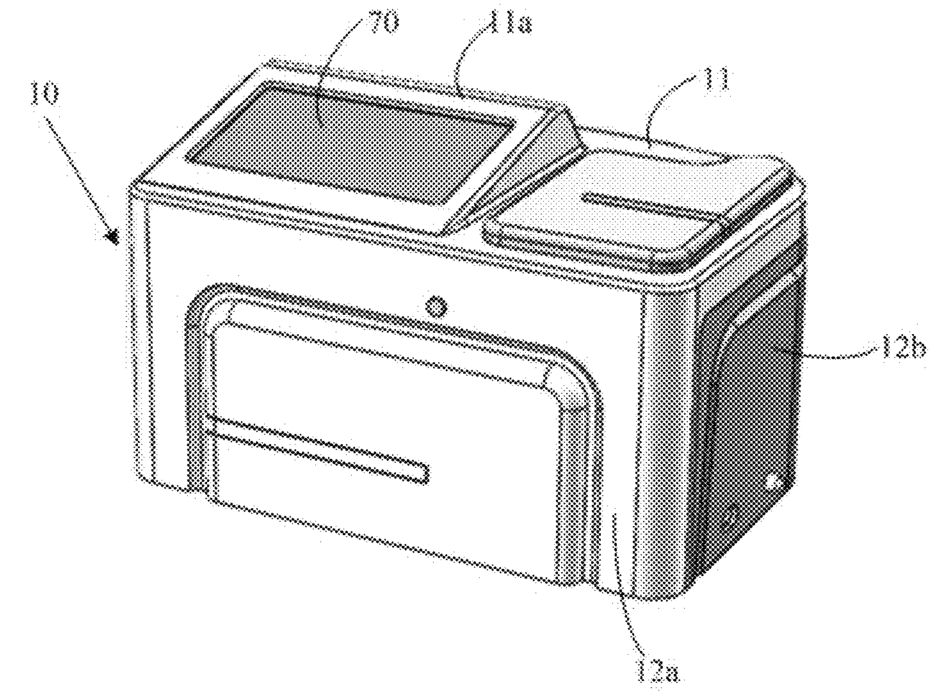
FIG. 1 is one schematic structural diagram illustrating an overall appearance of an immunoassay device according to some embodiments of the present disclosure.
Figure 2:
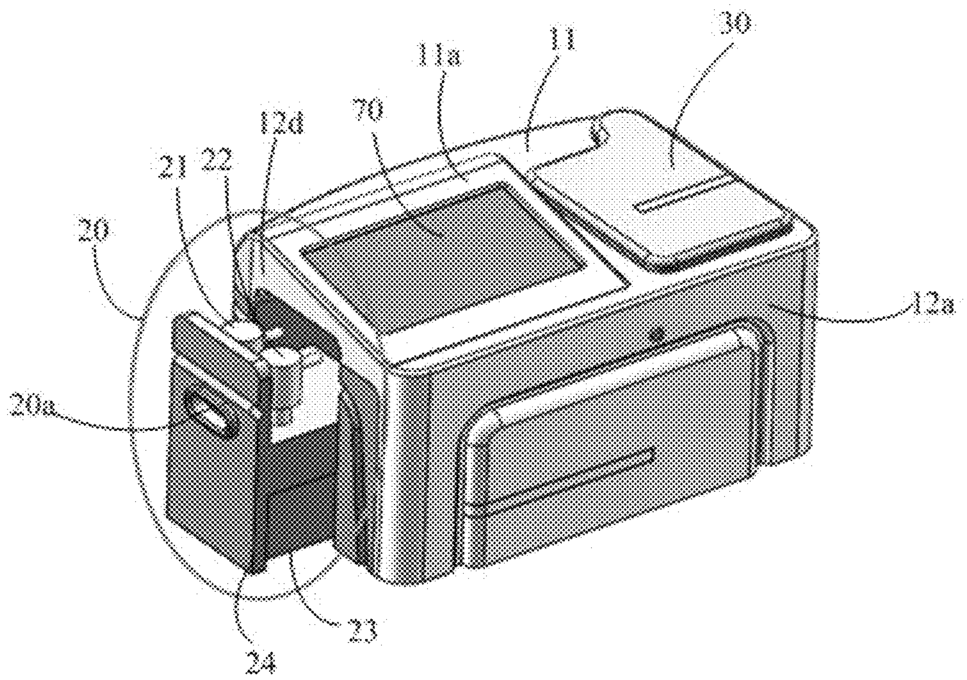
FIG. 2 is the another schematic structural diagram illustrating the overall appearance of the immunoassay device according to some embodiments of the present disclosure.
Figure 3:
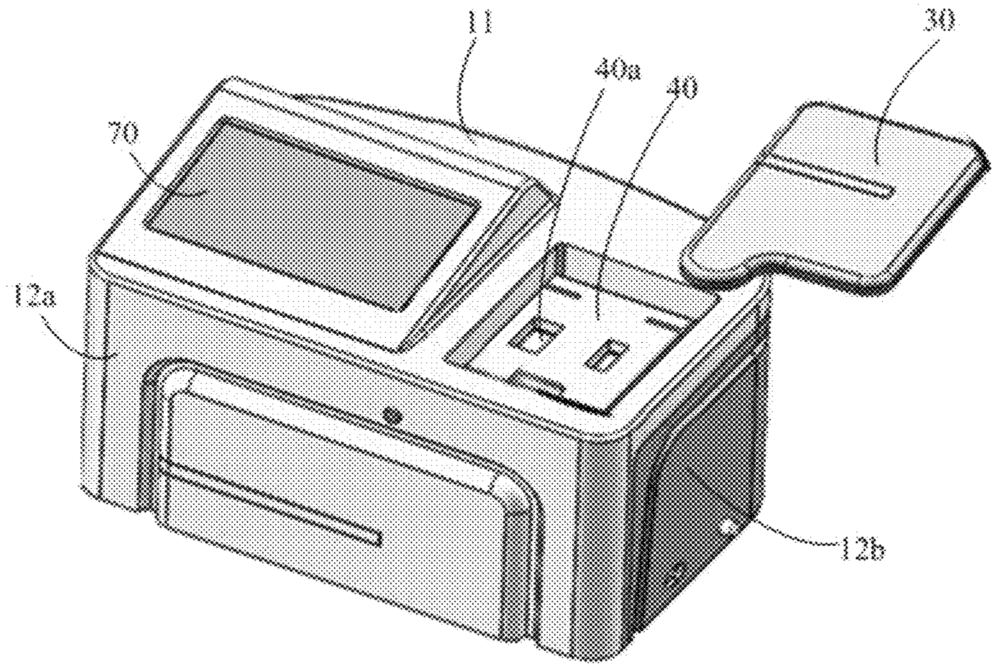
FIG. 3 is a schematic diagram of the immunoassay device according to some embodiments of the present disclosure, in which a cover plate is opened.
Figure 4A:
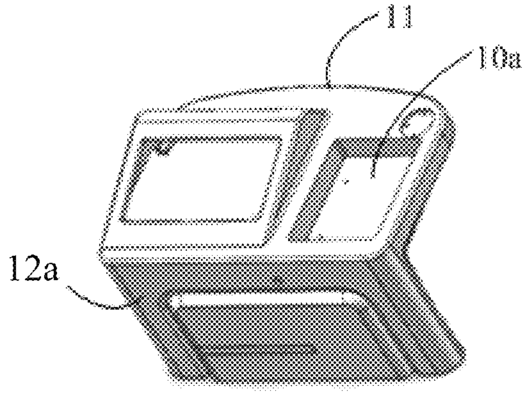
FIG. 4A is a schematic diagram of a portion of a housing of the immunoassay device according to some embodiments of the present disclosure.
Figure 4B:
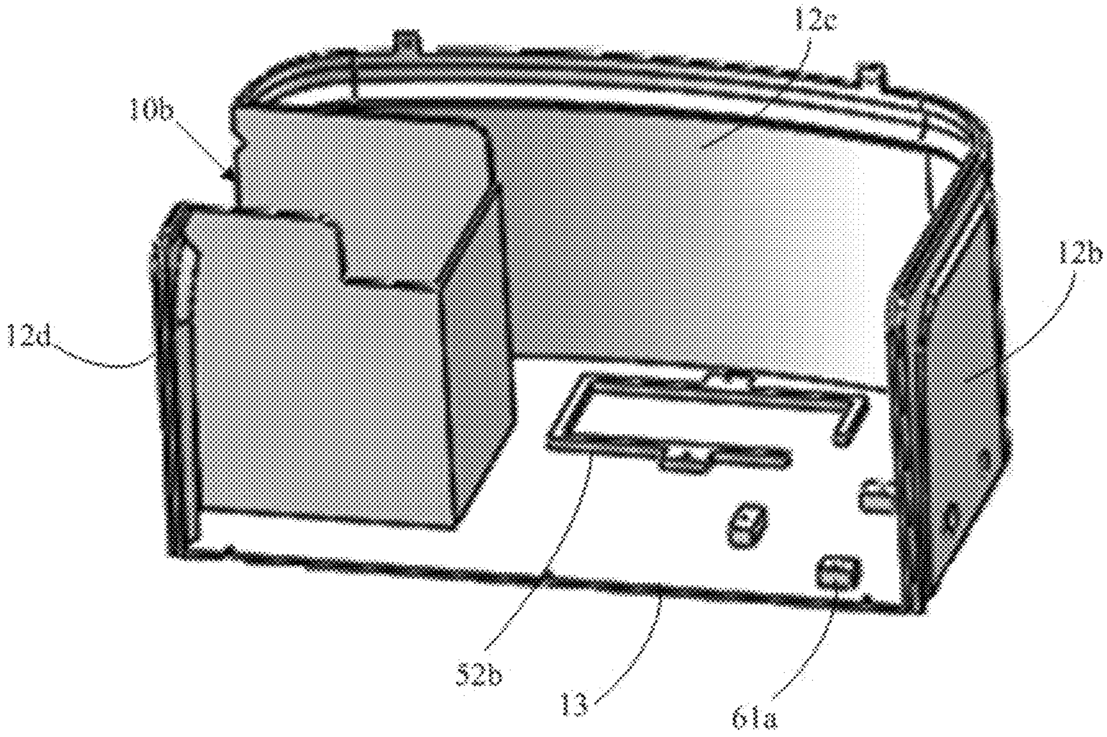
FIG. 4B is a schematic diagram of the another portion of the housing of the immunoassay device according to some embodiments of the present disclosure.
Figure 4C:
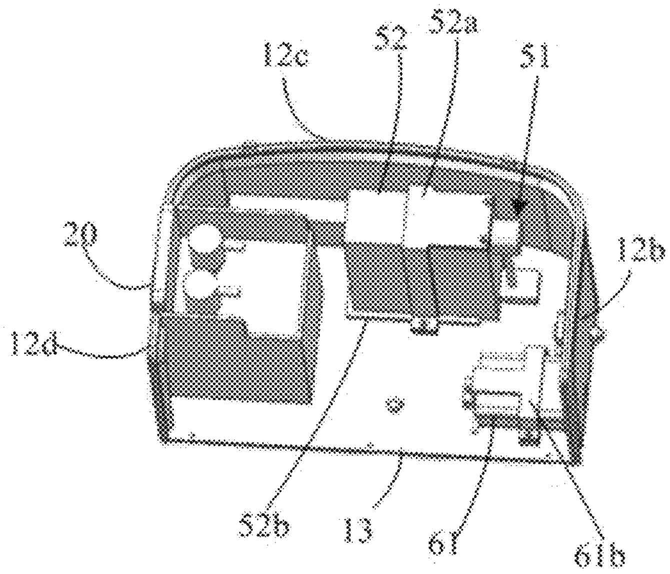
FIG. 4C is a schematic diagram of a partial structure of the immunoassay device according to some embodiments of the present disclosure.

FIG. 1 is one schematic structural diagram illustrating an overall appearance of an immunoassay device according to some embodiments of the present disclosure. FIG. 2 is the another schematic structural diagram illustrating the overall appearance of the immunoassay device according to some embodiments of the present disclosure. FIG. 3 is a schematic diagram of the immunoassay device according to some embodiments of the present disclosure, in which a cover plate is opened. FIG. 4A is a schematic diagram of a portion of a housing of the immunoassay device according to some embodiments of the present disclosure. FIG. 4B is a schematic diagram of another portion of the housing of the immunoassay device according to some embodiments of the present disclosure. FIG. 4C is a schematic diagram of a partial structure of the immunoassay device according to some embodiments of the present disclosure, and FIG. 4C shows a partial structure inside the housing. As shown in FIGS. 1 to 4B, the immunoassay device includes: a housing 10, a driving assembly, a detection chip (not shown), and a liquid storage chamber 20.

The detection chip is configured to perform an immunoassay. For example, the detection chip includes a substrate and a first cover plate, which are oppositely disposed and connected. The substrate may be a glass substrate, and the first cover plate may be a cover plate made of organic material. A groove is formed in the first cover plate. The substrate and the groove define a fluid channel. The cover plate is further provided with a liquid inlet and a liquid outlet, which communicate with the fluid channel. The fluid channel includes a first reaction zone and a second reaction zone in communication with each other. Freeze-dried powder of a fluorescent antibody is preset in the first reaction zone; the substrate in the second reaction zone makes capture antibody stay on the surface of the glass substrate by chemical modification. The chemical modification is, for example, silica connected with carboxyl group on the surface by reaction, and the carboxyl group being connected with the capture antibody. During the immunoassay, a sample solution with antigen enters the first reaction zone from the liquid inlet of the detection chip, and the antigen is connected to the fluorescent antibody to form a complex. The complex is captured by the capture antibody after entering the second reaction zone, and the rest fluorescent antibody is washed away by rinsing liquid. Thereafter, a concentration of the antigen is obtained by optical detection.

The housing 10 has a first accommodating part 10*a* and a second accommodating part 10*b*, and the detection chip is disposed in the first accommodating part 10*a*. For example, a chip fixing structure may be disposed in the first accommodating part 10*a*, and the detection chip may be fixed by the chip fixing structure. Optionally, the first accommodating part 10*a* may be an accommodating structure disposed on an outer surface of the housing 10, for example, the first accommodating part 10*a* is a groove disposed on an outer surface of the housing 10.

The liquid storage chamber 20 is disposed in the second accommodating part 10*b*. The liquid storage chamber 20 is configured at least to store reagent. The reagent may be the above-mentioned rinsing liquid. During the immunoassay of the detection chip, the rinsing liquid can wash away the fluorescent antibody that is not captured by the capture antibody. For example, the liquid storage chamber 20 may include a liquid tank for accommodating the reagent. Of course, the liquid storage chamber 20 may further include a liquid tank configured to accommodate waste liquid discharged from the detection chip. For example, the liquid storage chamber 20 includes a first liquid tank 21 and a second liquid tank 22. The first liquid tank 21 has a liquid outlet which is also a liquid outlet of the liquid storage chamber 20. The liquid outlet of the first liquid tank 21 communicates with the liquid inlet of the detection chip through a driving assembly. The first liquid tank 21 is configured to provide the reagent for the detection chip. The second liquid tank 22 has a liquid inlet which is also a liquid inlet of the liquid storage chamber 20. The liquid inlet of the second liquid tank 22 communicates with the liquid outlet of the detection chip. The second liquid tank 22 is configured to store the waste liquid discharged from the detection chip.

The driving assembly may be disposed inside the housing 10. The driving assembly is configured to communicate the liquid outlet of the liquid storage chamber 20 with the liquid inlet of the detection chip. The driving assembly is also configured to drive the reagent in the liquid storage chamber 20 into the detection chip. The driving assembly may control the amount of the reagent delivered to the detection chip from the liquid storage chamber 20.

In the embodiment of the present disclosure, the driving assembly may be utilized to drive the reagent in the liquid storage chamber 20 into the detection chip, thereby facilitating quantitative control of the reagent amount delivered to the detection chip. The liquid storage chamber 20 and the detection chip are both disposed in the accommodating part of the housing 10, so that the whole immunoassay device is more convenient to carry.

The immunoassay device of the present disclosure will be described in detail below with reference to the accompanying drawings. The immunoassay device is a portable device. Specifically, the housing 10 has a length between 25 cm and 40 cm, a width between and 30 cm, and a height between 15 cm and 25 cm. A dimension of the detection chip is between 70 mm and 80 mm in length, between 20 cm and 30 cm in width and between 1.0 mm and 2.0 mm in thickness. For example, the housing 10 has a length of 33 cm, a width of 22.5 cm, and a height of 20.8 cm; the detection chip has a length of a width of 25 mm and a thickness of 1.5 mm.

As shown in FIGS. 4A to 4C, the housing 10 includes: a top wall 11 and a bottom wall 13 disposed opposite to each other, and a side wall connected between the top wall 11 and the bottom wall 13. The top wall 11, the bottom wall 13 and the side wall enclose an accommodating space. For example, the side wall includes a first side wall portion 12*a*, a second side wall portion 12*b*, a third side wall portion 12*c* and a fourth side wall portion 12*d* connected in sequence. The first side wall portion 12*a* is disposed opposite to the third side wall portion 12*c*, and the second side wall portion 12*b* is disposed opposite to the fourth side wall portion 12*d*. The top wall 11 and the first side wall portion 12*a* may be formed as an integral structure, and the second side wall portion 12*b*, the third side wall portion 12*c*, the fourth side wall portion 12*d* and the bottom wall 13 may be formed as an integral structure. The first accommodating part 10*a* is a first groove disposed on the top wall 11, and the first groove is located on a side of the top wall 11 away from the bottom wall 13. The detection chip is positioned in the first groove. In one example, the first groove is disposed at a position of the top wall 11 close to the second side wall portion 12*b*.

In addition, a cover plate 30 may be further disposed on the housing 10, and the cover plate 30 defines a darkroom together with the first groove, so as to provide a light-shielding environment for the detection chip, thereby preventing the reaction process in the detection chip from being influenced by external light, and further improving the detection accuracy. The cover plate 30 may be connected to the top wall 11 in a hinged manner so as to open or close the darkroom. Specifically, the cover plate 30 may be connected to the top wall 11 by rotating hinge, so as to open or close the darkroom by rotating the cover plate to left or right on a plane approximately parallel to the top wall 11. Of course, the cover plate may also be connected to the top wall 11 in other manners. For example, magnetic attraction members are disposed on both the top wall 11 and the cover plate 30, and the cover plate 30 is detachably connected to the top wall 11 by magnetic attraction.

Figure 5A:
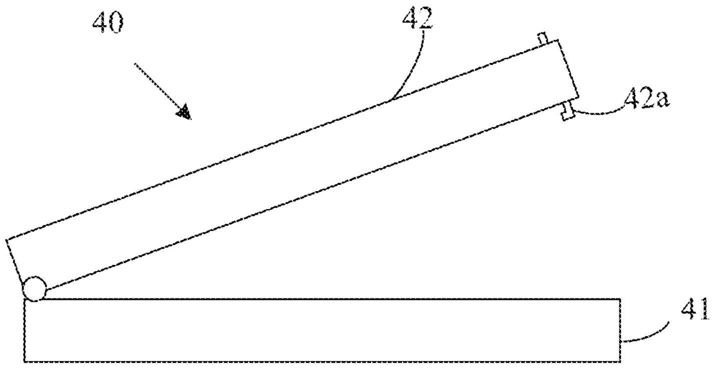
FIG. 5A is a side view of a chip clamp according to some embodiments of the present disclosure.
Figure 5B:
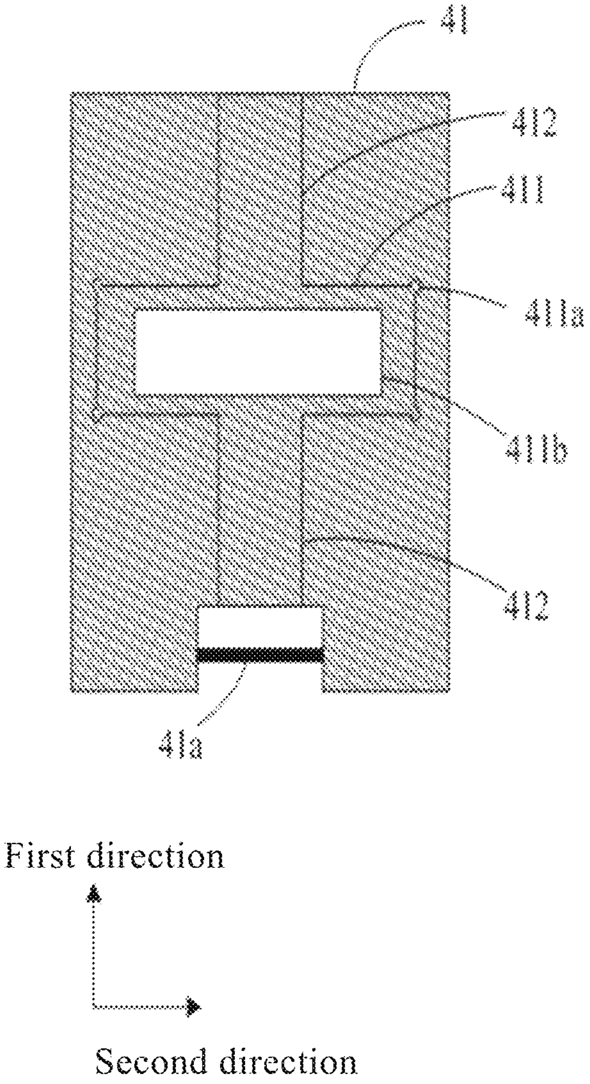
FIG. 5B is a plan view of a first clamping portion of the chip clamp according to some embodiments of the present disclosure.
Figure 5C:
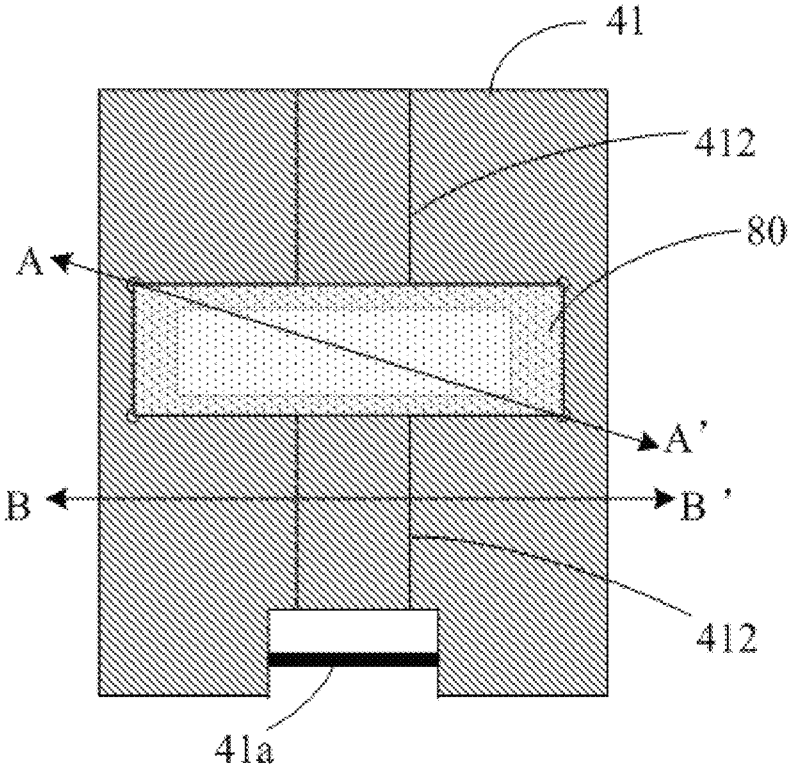
FIG. 5C is a plan view of the first clamping portion with the detection chip disposed on the first clamping portion.
Figure 5D:
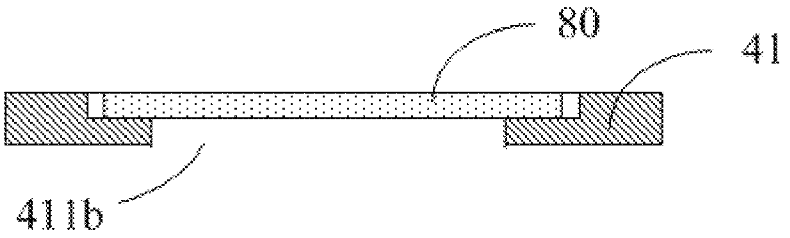
FIG. 5D is a sectional view taken along line A-A' in FIG. 5C.
Figure 5E:
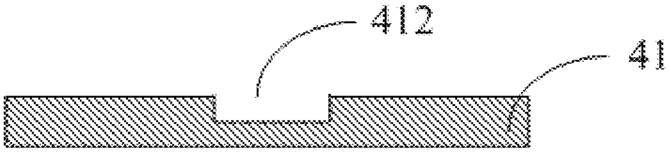
FIG. 5E is a sectional view taken along line B-B' of FIG. 5C.
Figure 5F:
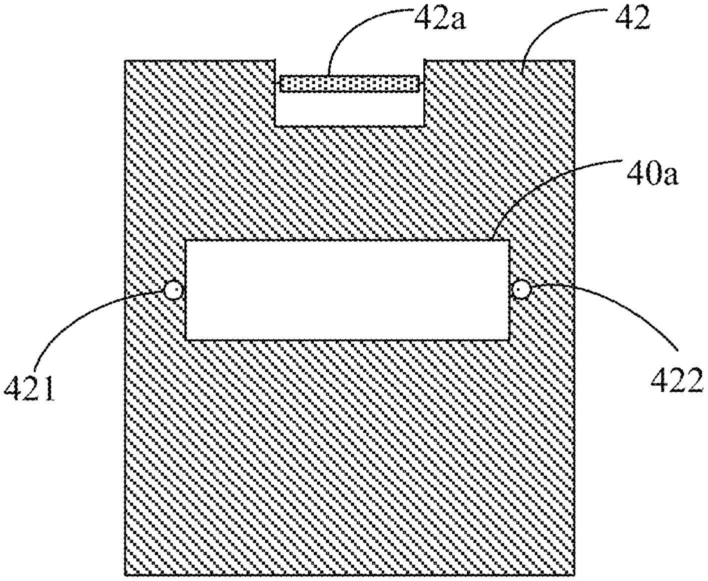
FIG. 5F is a plan view of a second clamping portion of the chip clamp according to some embodiments of the present disclosure.

As shown in FIGS. 3 and 4A, a chip clamp 40 is disposed in the first accommodating part and configured to clamp the detection chip, so that the detection chip remains fixed during the detection process. FIG. 5A is a side view of a chip clamp according to some embodiments of the present disclosure. FIG. 5B is a plan view of a first clamping portion of the chip clamp according to some embodiments of the present disclosure. FIG. 5C is a plan view of the first clamping portion with the detection chip disposed on the first clamping portion. FIG. 5D is a sectional view taken along line A-A' in FIG. 5C. FIG. 5E is a sectional view taken along line B-B' of FIG. 5C. FIG. 5F is a plan view of a second clamping portion of the chip clamp according to some embodiments of the present disclosure. As shown in FIGS. 5A to 5F, the chip clamp 40 includes a first clamping portion 41 and a second clamping portion 42 hinged to each other by a hinge (e.g., a hinge shaft), so that the chip clamp 40 can be switched between a clamping state and a release state. When the chip clamp 40 is in the clamping state, the detection chip 80 can be clamped; and when the chip clamp 40 is in the release state, the detection chip can be picked and placed.

A second groove 411 is disposed on a surface of the first clamping portion 41 facing the second clamping portion 42, and the second groove 411 is configured to accommodate the detection chip 80. The shape of the second groove 411 fits with the shape of the detection chip 80, so as to prevent the detection chip 80 in the second groove 11 from moving on the plane where it is located.

It should be noted that, although the shape of the second groove 411 fits with the shape of the detection chip 80, the shape of the second groove is not required to be exactly the same as the shape of the detection chip 80, as long as the position of the detection chip can be limited. For example, the detection chip 80 is a rectangular chip, the minimum distance of the second groove 411 in a first direction is substantially equal to a width of the detection chip 80, the minimum distance of the second groove 411 in a second direction is substantially equal to a length of the detection chip 80, and the first direction being perpendicular to the second direction. In this way, when the detection chip 80 is placed in the second groove 411, and the length direction of the detection chip 80 is parallel to the first direction and the width direction of the detection chip 80 is parallel to the second direction, the detection chip 80 can be stably disposed in the second groove 411 without moving along the plane where the detection chip is located.

In one example, as shown in FIGS. 5A to 5F, the detection chip 80 is a rectangular chip, arc processing is performed at positions of the second groove 411 corresponding to corners of the detection chip 80, so as to form arc relief portions 411*a*, which is advantageous for the manufacturing process of the second groove 411. When the detection chip 80 is placed in the second groove 411, the design of the arc relief portion 411*a* can prevent the corners of the detection chip 80 from being bumped.

In addition, at least two third grooves 412 are further disposed on the surface of the first clamping portion 41 facing the second clamping portion 42. The third grooves 412 are disposed on two opposite sides of the second groove 411, and the third grooves 412 communicate with the second groove 411. As such, an operator can conveniently place the detection chip 80 into the second groove 411 or take the detection chip 80 out of the second groove 411.

In one example, as shown in FIGS. 5B and 5C, the bottom of the second groove 411 may be provided with a hollowed-out pattern 411*b*, and an area of the hollowed-out pattern 411*b* is smaller than an area of the detection chip 80.

As shown in FIG. 2 and FIGS. 5A to 5F, the second clamping portion 42 is provided with a first opening and a second opening. A first sealing member 421 may be disposed in the first opening, and a second sealing member 422 may be disposed in the second opening. The first sealing member 421 has a first through hole, and the second sealing member 422 has a second through hole. The first through hole has a first top end opening and a first bottom end opening. The first bottom end opening is an opening of the first through hole close to the detection chip 80, and the first top end opening is an opening of the first through hole away from the detection chip 80. The second through hole has a second top end opening and a second bottom end opening. The second bottom end opening is an opening of the second through hole close to the detection chip 80, and the second top end opening is an opening of the second through hole away from the detection chip 80. The first top end opening of the first through hole may communicate with the driving assembly through a connecting hose, and the first top end opening of the second through hole may communicate with the liquid inlet of the liquid storage reservoir 20 through a connecting hose. When the chip clamp 40 is in the clamping state, both the first sealing member 421 and the second sealing member 422 are in close contact with the detection chip 80. An orthographic projection of the first bottom end opening of the first through hole on the detection chip 80 overlaps with an area where the liquid inlet of the detection chip 80 is located, and an orthographic projection of the first bottom end opening of the second through hole on the detection chip 80 overlaps with an area where the liquid outlet of the detection chip 80 is located, thereby communicating the first bottom end opening of the first through hole with the liquid inlet of the detection chip 80, and communicating the second bottom end opening of the second through hole with the liquid outlet of the detection chip 80, so that the driving assembly can communicate with the liquid inlet of the detection chip 80 through the first through hole, and the liquid inlet of the liquid storage reservoir 20 communicate with the liquid outlet of the detection chip 80 through the second through hole.

It should be noted that the term "close contact" means that the contact surfaces of the two structures are in direct contact with each other without any gap allowing a liquid to flow. By the arrangement of the first sealing member 421 and the second sealing member 422, the reagent can be prevented from leaking in the process of entering the detection chip 80 or flowing out of the detection chip 80.

In some embodiments, the first through hole and the second through hole may be both cylindrical through holes. That is, the first top end opening and the first bottom end opening of the first through hole have the same size, and the second top end opening and the second bottom end opening of the second through hole have the same size.

In some embodiments, when the chip clamp 40 is in the clamping state, the area where the liquid inlet of the detection chip 80 is located is within an orthographic projection range of the first bottom end opening of the first through hole on the detection chip 80, and the area where the liquid outlet of the detection chip 80 is located is within an orthographic projection range of the second bottom end opening of the second through hole on the detection chip 80. In this case, the first through hole and the liquid inlet of the detection chip 80 may form a funnel-shaped structure as a whole, so that the reagent can enter the liquid inlet of the detection chip 80 rapidly, and the liquid outlet of the detection chip 80 can discharge waste liquid to the second through hole smoothly.

Illustratively, the opening diameters (calibers) of the liquid inlet and the liquid outlet of the detection chip 80 are both between 0.8 mm and 1.2 mm; the opening diameters of the first bottom end opening of the first through hole and the second bottom end opening of the second through hole are both between 1 mm and 1.5 mm. For example, the opening diameters of the liquid inlet and the liquid outlet of the detection chip 80 are both 1 mm, and the opening diameters of the first bottom end opening of the first through hole and the second bottom end opening of the second through hole are both 1.2 mm, so that the reagent can enter the liquid inlet of the detection chip 80 rapidly, which facilitates accurate control of the amount of reagent entering the detection chip 80.

In other embodiments, when the chip clamp 40 is in the clamping state, an orthographic projection of the first bottom end opening of the first through hole on the detection chip 80 is within an area where the liquid inlet of the detection chip 80 is located, and an orthographic projection of the second bottom end opening of the second through hole on the detection chip 80 is within an area where the liquid outlet of the detection chip 80 is located. In this case, the reagent provided by the liquid storage reservoir 20 can enter the liquid inlet of the detection chip 80 smoothly.

In some embodiments, the first sealing member 421 and the second sealing member 422 are each an elastic member capable of being elastically deformed. Specifically, the elastic member may be made of material such as plastic, rubber, or silicone. When the chip clamp 40 is in the release state, the first sealing member 421 and the second sealing member 422 may protrude out of an inner surface of the second clamping portion 42 (i.e., a surface of the second clamping portion 42 facing the first clamping portion 41); when the chip clamp 40 is in the clamping state, the first sealing member 421 and the second sealing member 422 are each in a compressed state. The following effect can be realized by the above setting: when the chip clamp 40 is in the clamping state, the first sealing member 421 and the second sealing member 422 are both in close contact with the detection chip 80 without scratching the detection chip 80.

The shape of the first sealing member 421 and the second sealing member 422 is not particularly limited in the embodiments of the present disclosure. For example, the first sealing member 421 and the second sealing member 422 are cylindrical. Alternatively, the first sealing member 421 and the second sealing member 422 are both conical, and when the chip clamp 40 is in the release state, the bottom of the conical shape protrudes out of the inner surface of the second clamping portion 42. Alternatively, the first sealing member 421 and the second sealing member 422 are in the shape of a truncated cone, and when the chip clamp 40 is in the release state, the bottom of the truncated cone protrudes out of the inner surface of the second clamping portion 42. Alternatively, the first sealing member 421 and the second sealing member 422 each include two cylindrical sealing bodies, one of the sealing bodies of the first sealing member 421 is located in the first opening, and the other of the sealing bodies of the first sealing member 421 protrudes out of the first opening; one of the sealing bodies of the second sealing member 422 is located in the second opening, and the other of the sealing bodies of the second sealing member 422 protrudes out of the second opening.

As shown in FIG. 4F, the second clamping portion 42 is provided with a light-passing portion 40*a*. The light-passing portion 40*a* corresponds to the reaction zone on the detection chip 80, so that the reaction result in the reaction zone of the detection chip 80 can be optically observed without opening the chip clamp 40. A hollowed-out structure may be disposed on the second clamping portion 42, and the hollowed-out structure serves as the light-passing portion 40*a*. In addition, the light-passing portion 40*a* may be provided in one or in plural.

As described above, the first clamping portion 41 and the second clamping portion 42 are hinged by a hinge. In order to enable the chip clamp to stably clamp the detection chip 80 in the clamping state, an end of the first clamping portion 41 away from the hinged position and an end of the second clamping portion 42 away from the hinged position may be detachably connected. In some embodiments, the end of the first clamping portion 41 away from the hinged position is provided with a connecting member 41*a*, and the end of the second clamping portion 42 away from the hinged position is provided with an engaging member 42*a*. The connecting member 41*a* engages with the engaging member 42*a* when the chip clamp 40 is in the clamping state. The embodiment of the present disclosure does not limit the specific structural form of the connecting member 41*a* and the engaging member 42*a*, as long as the connecting member 41*a* and the engaging member 42*a* can be engaged with each other. For example, as shown in FIGS. 5A to 5F, a notch is disposed on a side of the first clamping portion 41 away from the hinged position, the connecting member 41*a* is a cross bar disposed at the notch, and the engaging member 42*a* is a hook engaged with the cross bar. Of course, the end of the first clamping portion 41 away from the hinged position may be detachably connected to the end of the second clamping portion 42 away from the hinged position by other connecting structures. For example, magnetic members are disposed at the end of the first clamping portion 41 away from the hinged position and the end of the second clamping portion 42 away from the hinged position.

In some embodiments, the first clamping portion 41 may be fixed to the bottom of the first accommodating part 10*a* by a fixing member. The bottom of the first accommodating part 10*a* may be provided with a through hole, and the through hole is disposed outside an area covered by the chip clamp 40. In this way, the connecting hose connected to the liquid inlet of the detection chip 80 can pass through the through hole to be connected with the driving assembly, and the connecting hose connected to the liquid outlet of the detection chip 80 can pass through the through hole to be connected with the liquid inlet of the liquid storage reservoir.

In some embodiments, as shown in FIG. 4C, the driving assembly may specifically include: a controller (not shown), a driver and a conveyer 51, wherein the controller being connected to the driver 52 and the driver 52 being connected to the conveyer 51. The controller is configured to send a control signal to the driver 52, and the control signal is intended to control the driver 52 to provide a corresponding driving action for the conveyer 51, so as to drive the conveyer 51 to generate a corresponding action, thereby controlling the reagent to flow. The controller may use a demoboard, and a controller mounting plate may be disposed in an accommodating space inside the housing 10. The controller mounting plate is fixed to the first side wall portion 12*a* of the housing 10, and the controller is fixed to the controller mounting plate 53.

Figure 6:
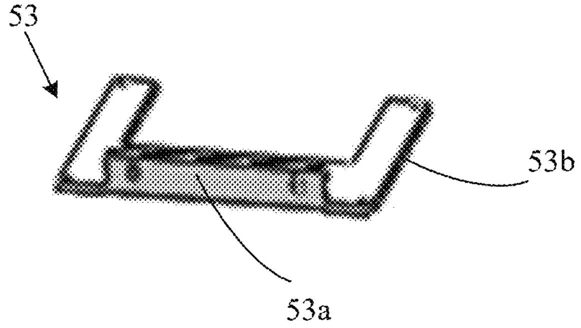
FIG. 6 is a schematic diagram of a controller mounting plate according to some embodiments of the present disclosure.

FIG. 6 is a schematic diagram of a controller mounting plate according to some embodiments of the present disclosure. As shown in FIG. 6, the controller mounting plate 53 may include: a first mounting portion 53*a* and a second mounting portion 53*b*. The first mounting portion 53*a* is fixedly connected to the second mounting portion 53*b*. For example, the first mounting portion 53*a* and the second mounting portion 53*b* are formed as an integral structure. As shown in FIGS. 3, 4C and 6, the first mounting portion 53*a* is mounted on the first side wall portion 12*a* of the housing 10 by a connecting member such as a screw; the second mounting portion 53*b* is configured to fix the controller. The shape of the second mounting portion 53*b* is not limited. For example, the second mounting portion 53*b* may have a U-shaped structure or a frame shape structure. For example, the second mounting portion 53*b* may be substantially parallel to the bottom wall 13 of the housing 10.

As shown in FIGS. 4B and 4C, the driver 52 may specifically use a stepping motor, which generates a corresponding stepping action in response to a control signal of the controller. The driver 52 may be fixed to the bottom wall 13 of the housing 10 by a fixing member. In some embodiments, the driver 52 and the conveyor 51 may be disposed at a position close to the third side wall portion 12*c*, and the conveyor 51 is located at a side of the driver 52 close to the second side wall portion 12*b*. For example, a position limiter 52*b* is fixedly disposed on the bottom wall 13 at a position close to the third side wall portion 12*c*, and the driver 52 and the conveyor 51 are disposed within a range defined by the position limiter 52*b*. For example, a driver mounting member 52*a* is sleeved on the housing of the driver 52, and the driver mounting member 52*a* is connected to the position limiter 52*b* so as to fix the driver 52 to the bottom wall 13.

Figure 7:
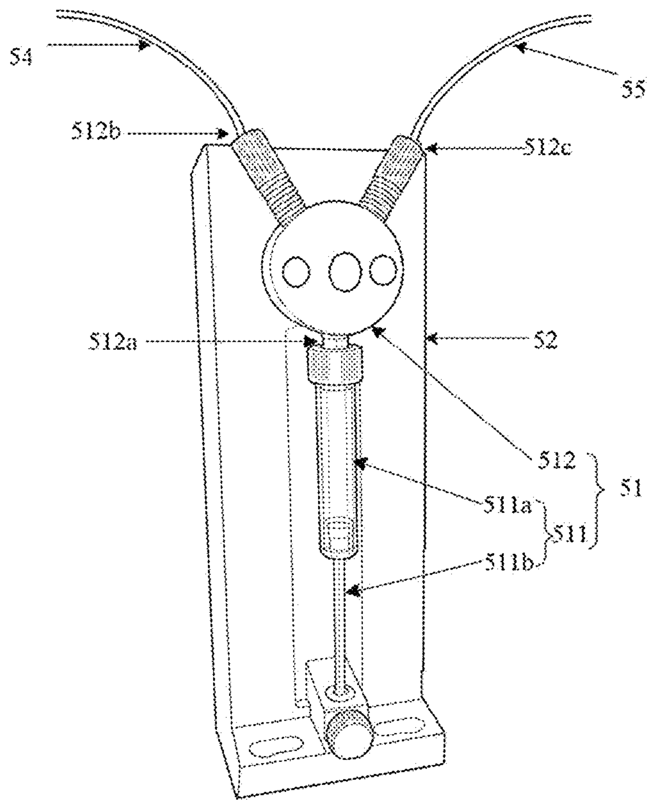
FIG. 7 is a schematic diagram of a driver and a conveyor according to some embodiments of the present disclosure.

FIG. 7 is a schematic diagram of the driver and the conveyor according to some embodiments of the disclosure. As shown in FIG. 7, the conveyor 51 includes a flow direction regulating member 512 and a syringe pump 511, and the syringe pump 511 communicates with the liquid outlet of the liquid storage reservoir and the liquid inlet of the detection chip, so as to pump the reagent from the liquid storage reservoir and provide the pumped reagent to the detection chip. The syringe pump 511 includes: a pump body 511*a* and a piston rod 511*b*. The pump body 511*a* may be a cylindrical structure that includes a first pump port and a second pump port. The piston rod 511*b* has a piston end and an actuating end. The actuating end of the piston rod 511*b* is connected to the driver 52, and the piston end is provided with a piston. The piston end extends into the pump body 511*a* from the first pump port, and the second pump port is configured to suck or discharge the reagent. The piston rod 511*b* is moved under control by the driver 52, so as to cause the pump body 511*a* to suck or discharge the reagent through the second pump port.

The flow direction regulating member 512 has a first opening 512*a*, a second opening 512*b* and a third opening 512*c*. The first opening 512*a* communicates with the second pump port of the syringe pump 511, the second opening 512*b* communicates with the liquid inlet of the detection chip through a hose 54, and the third opening 512*c* communicates with the liquid outlet of the liquid storage chamber 20 through a hose 55. The flow direction regulating member 512 is configured to communicate one of the second opening 512*b* and the third opening 512*c* with the first opening 512*a* under drive by the driver 52. For example, when reagent needs to be provided to the detection chip, the third opening 512*c* of the flow direction regulating member 512 may be firstly controlled to communicate with the first opening 512*a*, so that the liquid outlet of the liquid storage reservoir communicates with the second opening 512*b* of the syringe pump 511. The piston rod 511*b* is driven to move in a direction away from the second pump port, so that the liquid in the liquid storage reservoir is pumped into the pump body 511*a*. Thereafter, the second opening 512*b* of the flow direction regulating member is controlled to communicate with the first opening 512*a*, so that the second pump port of the syringe pump 511 communicates with the liquid inlet of the detection chip. The piston rod 511*b* is driven to move in a direction close to the second opening 512*b*, thereby outputting the reagent in the syringe pump 511 to the detection chip. In the embodiment of the present disclosure, by controlling the moving distance of the piston rod 511*b* of the syringe pump 511, the amount of the reagent output to the detection chip can be accurately controlled.

In some embodiments, the controller may send a series of control signals to the driver 52 according to a preset program, so as to control the driver 52 to generate a corresponding driving action, and thus completing the detection process automatically. Of course, parameters may also be input by a user to the controller according to actual needs, so that the controller sends corresponding control signals according to the parameters input by the user.

As shown in FIGS. 1 and 2, the immunoassay device may further include a display 70 disposed on a side of the top wall 11 close to the bottom wall 13. Further, the display may be disposed at a position close to the fourth side wall portion 12*d*. For example, a convex portion 11*a* is formed on the top wall 11 at a position close to the fourth side wall portion 12*d*, the convex portion 11*a* protrudes in a direction away from the bottom wall 13, and the display 70 is located on a side of the convex portion 11*a* facing the bottom wall 13. A hollowed-out portion is disposed on the convex portion 11*a* of the top wall 11, and the hollowed-out portion exposes a display area of the display 70. The present disclosure does not limit the manner in which the display 70 is fixed, as long as the display 70 and the housing 10 can remain fixed. For example, a mounting plate may be disposed on a side of the convex portion 11*a* close to the bottom wall 13, the mounting plate is fixedly connected to the convex portion 11*a* by a detachable connecting member such as a screw, and the display 70 is sandwiched between the convex portion 11*a* and the fixing plate.

The display 70 is configured to display driving parameters of the driving assembly, for example, the driving parameters may include actions of the syringe pump 511, including: movement times of the piston rod 511*b*, direction of each movement, distance of movement, and the like.

The display 70 may include a touch display screen, so that parameters may be input or modified by touch. Of course, the parameters may also be input or modified by an external input device.

In some embodiments, a power supply assembly is further disposed in the accommodating chamber inside the housing 10 to supply power for the driving assembly and the display 70. As shown in FIG. 4C, the power supply assembly may be disposed at a position close to the second side wall portion 12*b*. The power supply assembly may specifically include: a first power supply 61 and a second power supply (not shown), the first power supply 61 being configured to power the controller and display 70, and the second power supply being configured to power the driver 52. For example, the voltage of the first power supply 61 is around 12V and the voltage of the second power supply is around 24V. As shown in FIGS. 4B and 4C, a first fixing member 61*a* is disposed on the bottom wall 13 of the housing 10, and the first fixing member 61*a* is disposed at a position close to the second side wall portion 12*b*. The first power supply 61 is sleeved with a second fixing member 61*b*, and the first fixing member 61*a* is connected to the second fixing member 61B, so as to fix the first power supply 61 to the bottom wall 13. The same fixing manner may also apply to the second power supply.

As described above, the liquid storage chamber 20 is disposed in the second accommodating part 10*b*, and the liquid storage chamber 20 is configured at least to store reagent. In some embodiments, as shown in FIG. 4B, the second accommodating part 10*b* is disposed on the fourth side wall portion 12*d*. For example, a part of the fourth side wall portion 12*d* is recessed into the housing 10 to form the second accommodating part 10*b*, which can make the whole device structure more compact, thereby improving the portability. The liquid storage chamber 20 can be moved into or out of the second accommodating part 10*b*.

Figure 8:
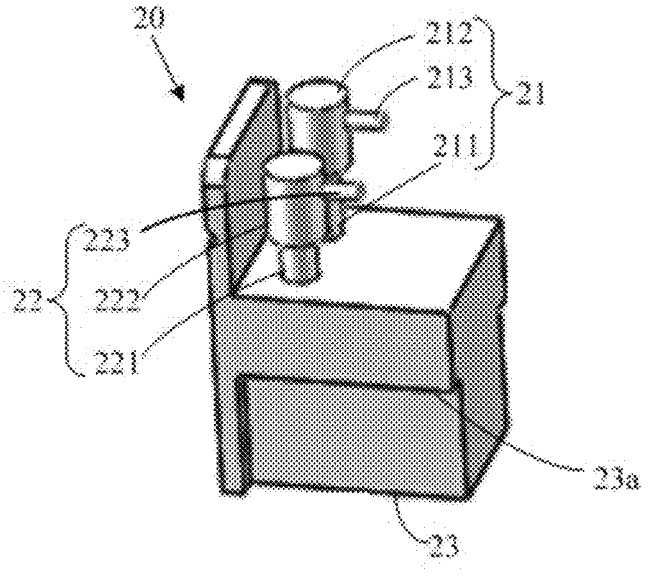
FIG. 8 is a schematic diagram of a liquid storage chamber according to some embodiments of the present disclosure.

FIG. 8 is a schematic diagram of a liquid storage chamber according to some embodiments of the present disclosure. As shown in FIG. 8, the liquid storage chamber includes: a body part 23, a first liquid tank 21 and a second liquid tank 22. The first liquid tank 21 and the second liquid tank 22 are disposed on the body part 23. As shown in FIGS. 2 and 8, a second guide portion 23*a* is disposed on the body part 23. A first guide portion (not shown), which cooperates with the second guide portion 23*a*, is disposed on an inner wall of the second accommodating part 10*b*. The second guide portion 23*a* is configured to move along the first guide portion, thereby moving the liquid storage chamber 20 into or out of the second accommodating part 10*b*.

The specific structure of the first guide portion and the second guide portion 23*a* is not limited in the embodiment of present disclosure. For example, the first guide portion may be a raised strip disposed on the inner wall of the second accommodating part 10*b*, and the second guide portion may be a groove disposed on the body part 23 For another example, the first guide portion is a slide rail disposed on the inner wall of the second accommodating part 10*b*, and the second guide portion is a slider disposed on the body part 23.

The body part 23 may further include a baffle plate 24. When the body part 23 is moved into the second accommodating part 10*b*, a surface of the baffle plate 24 away from the body part 23 may be substantially on the same plane as the fourth side wall portion 12*d*. A pulling portion 20*a* may be further disposed on the baffle plate 24, so as to facilitate the user to pull the liquid storage chamber 20 out of the second accommodating part 10*b*. The first liquid tank 21 is configured to store reagent. The liquid outlet of the first liquid tank 21 serves as the liquid outlet of the liquid storage chamber 20 to be connected with the liquid inlet of the detection chip. The liquid inlet of the second liquid tank 22 communicates with the liquid outlet of the detection chip. The second liquid tank 22 is configured to store waste liquid discharged from the detection chip. Optionally, the body part 23 is provided with a first mounting hole and a second mounting hole, wherein a part of the first tank 21 is inserted into the first mounting hole, and a part of the second tank 22 is inserted into the second mounting hole, so that the first liquid tank 21 and the second liquid tank 22 remain stabilized.

As shown in FIG. 8, the first liquid tank 21 may specifically include: a first liquid storage tube 211, and a first sealing cover 212 that is disposed at a tube orifice of the first liquid storage tube 211. The liquid outlet of the first liquid tank 21 is disposed on the first sealing cover 212. The liquid outlet of the first liquid tank 21 communicates with the interior of the first liquid storage tube 211 through a flow channel in the first sealing cover 212. The second liquid tank 22 may specifically include: a second liquid storage tube 221 and a second sealing cover 222. A liquid inlet of the second liquid tank 22 is disposed on the second sealing cover 222. The liquid outlet of the second liquid tank 22 communicates with the interior of the second liquid storage tube 221 through a flow channel in the second sealing cover 222. At least one of the first liquid storage tube 211 and the second liquid storage tube 221 includes a centrifuge tube.

The liquid outlet of the first liquid tank 21 serves as the liquid outlet of the liquid storage chamber 20, and is connected to the driving assembly through a connecting hose. The liquid inlet of the second liquid tank 22 serves as the liquid inlet of the liquid storage reservoir, and communicates with the liquid outlet of the detection chip through a connecting hose.

As shown in FIG. 5, a hollow first hose connecting portion 213 may be further disposed on the first sealing cover 212 of the first liquid tank 21. A hose connected to the first liquid tank 21 may be sleeved on the first hose connecting portion 213, so as to communicate with the liquid outlet of the first liquid tank 21 through the first hose connecting portion 213. Similarly, a second hose connecting portion 223 may be disposed on the second sealing cover 222 of the second liquid tank 22. A hose connected to the second liquid tank 22 may be sleeved on the second hose connecting portion, so as to communicate with the liquid outlet of the second liquid tank 22 through the second hose connecting portion. The first hose connecting portion 213 and the first sealing cover 212 may be of an integral structure, and the second hose connecting portion 223 and the second sealing cover 222 may be of an integral structure.

The embodiment of the present disclosure further provides an immunoassay method for an immunoassay device described above, and the method includes the following steps.

S11, adding a sample solution with antigen into a detection chip, so that at least a part of the antigen in the sample solution reacts with a fluorescent antibody preset in the detection chip, and a complex formed after reaction being captured by a capture object preset in the detection chip.

S12, utilizing the driving assembly to drive a liquid outlet of the liquid storage chamber to communicate with a liquid inlet of the detection chip, and drive the reagent in the liquid storage chamber to enter the detection chip, so as to wash away the fluorescent antibody that is not combined with the antigen.

Thereafter, observing the antigen in the reaction zone using a fluorescent reading device (e.g., a fluorescent microscope) for data analysis.

In one example, the immunoassay process using the immunoassay device described above includes the following steps.

S21, placing the detection chip in the chip clamp, and adding a sample solution to be detected into the liquid inlet of the detection chip using a liquid transfer chamber, the sample solution to be detected may include antigen.

S22, clamping the detection chip using the chip clamp, and closing the darkroom. Thereafter, the controller sends a control signal to the driver to make the driver to perform the following steps.

S23, driving the piston rod of the syringe pump to move upwards, so as to push the sample solution to the first reaction zone.

S24, controlling the first opening of the flow direction regulating member to communicate with the second pump opening of the syringe pump, and driving the piston rod of the syringe pump to move upwards and downwards, so that the sample solution in the detection chip moves back and forth in the first reaction zone, and the antigen in the sample solution is combined with the fluorescent antigen in the first reaction zone to form a complex.

That the piston rod moves upwards means that the piston rod moves close to a second pump port, and that the piston rod moves downwards means that the piston rod moves away from the second pump port. In one example, at step S24, the piston rod moves upwards each time by the same distance as it moves downwards each time. For example, the driver is a stepping motor, when the piston rod is driven to move upwards or downwards, the stepping motor steps by 200 steps. In one example, the driver drives the piston rod to alternately perform an upward movement and a downward movement for three times, and then the process goes to step S25.

S25, driving the piston rod of the syringe pump to move upwards so as to push the sample solution to the second reaction zone. For example, the stepping motor steps by 250 steps to drive the piston rod to move upwards.

S26, driving the piston rod of the syringe pump to move upwards and downwards, so that the sample solution in the detection chip moves back and forth in the second reaction zone, and the complex is combined with the capture antibody in the second reaction zone.

In one example, at step S26, the piston rod moves upwards each time by the same distance as it moves downwards each time. For example, the driver is a stepping motor, when the piston rod is driven to move upwards or downwards, the stepping motor steps by 200 steps. In one example, the driver drives the piston rod to alternately perform an upward movement and a downward movement for three times, and then the process goes to step S27.

S27, controlling the third opening of the flow direction regulating member to communicate with the second pump port of the syringe pump, and driving the piston rod of the syringe pump to move downwards, so that the syringe pump sucks the reagent from the liquid storage chamber.

S28, controlling the second opening of the flow direction regulating member to communicate with the second pump port of the syringe pump, and driving the piston rod of the syringe pump to move upwards, so that the sample solution in the syringe pump is injected into the detection chip, the reaction zone is cleaned, and the fluorescent antibody which does not react with the antigen is washed away.

A distance that the piston rod moves downwards in step S27 may be the same as a distance that the piston rod moves upwards in step S28. For example, when the piston rod of the syringe pump is driven to move downwards in step S27, the stepping motor steps by 5000 steps, and when the piston rod of the syringe pump is driven to move upwards in step S28, the stepping motor steps by 5000 steps.

S29, taking out the detection chip, analyzing data by fluorescence detection. For example, the antigen concentration is determined.

It should be understood that above embodiments are just exemplary implementations for illustrating the principle of the present disclosure, however, the present disclosure is not limited thereto. Various modifications and variations can be made by a person skilled in the art without departing from the scope of the present disclosure. These modifications and variations should be considered to be within protection scope of the present disclosure.

What is claimed is:

1. An immunoassay device, wherein the immunoassay device comprises: a housing, a driving assembly, a detection chip and a liquid storage chamber;

the detection chip is provided with a fluid channel, and a liquid inlet and a liquid outlet in communication with the fluid channel, wherein the fluid channel comprises a first reaction zone and a second reaction zone in communication with each other;

the housing has a first accommodating part and a second accommodating part, and the detection chip is disposed in the first accommodating part, and the liquid storage chamber is disposed in the second accommodating part, and the liquid storage chamber is configured at least to store reagent;

the driving assembly is configured to communicate a liquid outlet of the liquid storage chamber with the liquid inlet of the detection chip, and drive the reagent in the liquid storage chamber to enter the detection chip;

the housing comprises: a top wall and a bottom wall disposed opposite to each other, and a side wall connected between the top wall and the bottom wall, wherein the first accommodating part is disposed on a side of the top wall away from the bottom wall, the second accommodating part is formed on the side wall;

the driving assembly is disposed in a space enclosed by the top wall, the bottom wall and the side wall; and wherein a fixing plate is disposed on the side wall, and the driving assembly comprises a controller fixed to the fixing plate.

2. The immunoassay device of claim 1, wherein the driving assembly further comprises: a driver and a conveyer; the controller is connected to the driver, the driver is connected to the conveyer, and the controller is configured to control the driver to drive the conveyer so that the conveyer controls the reagent to flow from the liquid storage chamber to the detection chip and in the fluid channel of the detection chip.

3. The immunoassay device of claim 2, wherein the conveyer comprises: a flow direction regulating member and a syringe pump; wherein, the syringe pump comprises: a pump body and a piston rod, wherein a piston end of the piston rod extends into the pump body from a first pump port of the pump body, an actuating end of the piston rod is connected to the driver, and the piston rod moves under control by the driver, so that the syringe pump sucks or discharges the reagent through a second pump port; and the flow direction regulating member has a first opening, a second opening and a third opening, wherein the first opening communicates with the second pump port of the syringe pump, the second opening communicates with the liquid inlet of the detection chip, the third opening communicates with the liquid outlet of the liquid storage chamber, and the flow direction regulating member is configured to communicate one of the second opening and the third opening with the first opening under drive by the driver.

4. The immunoassay device of claim 1, wherein the first accommodating part is a first groove formed on the top wall, and the immunoassay device further comprises: a cover plate configured to define a darkroom with the first groove.

5. The immunoassay device of claim 4, wherein the cover plate is hinged to the top wall so as to open or close the darkroom.

6. The immunoassay device of claim 1, further comprising: a display disposed on a side of the top wall close to the bottom wall and configured to display driving parameters of the driving assembly; and a hollowed-out portion disposed on the top wall and exposing a display area of the display.

7. The immunoassay device of claim 1, wherein the liquid storage chamber comprises: a body part, a first liquid tank and a second liquid tank, the first liquid tank and the second liquid tank being disposed on the body part;

wherein the first liquid tank is configured to store the reagent, a liquid outlet of the first liquid tank serves as the liquid outlet of the liquid storage chamber; and a liquid inlet of the second liquid tank communicates with the liquid outlet of the detection chip, and the second liquid tank is configured to store waste liquid discharged from the detection chip.

8. The immunoassay device of claim 7, wherein the body part is provided with a first mounting hole and a second mounting hole, the first liquid tank is inserted into the first mounting hole, and a second mounting hole the second liquid tank is inserted into the first mounting hole.

9. The immunoassay device of claim 8, wherein the immunoassay device further comprising: a plurality of connecting hoses; the liquid inlet of the second liquid tank is connected to the liquid outlet of the detection chip by one connecting hose of the plurality of connecting hoses, and the liquid outlet of the first liquid tank is connected to the driving assembly by another one connecting hose of the plurality of connecting hoses;

wherein the first liquid tank comprises: a first liquid storage tube and a first sealing cover, wherein the liquid outlet of the first liquid tank is disposed on the first sealing cover and communicates with the first liquid storage tube through a flow channel in the first sealing cover; and the second liquid tank comprises: a second liquid storage tube and a second sealing cover, wherein the liquid inlet of the second liquid tank is disposed on the second sealing cover and communicates with the second liquid storage tube through a flow channel in the second sealing cover, wherein at least one of the first liquid storage tube and the second liquid storage tube comprises a centrifuge tube.

10. The immunoassay device of claim 7, wherein a first guide portion is disposed on an inner wall of the second accommodating part, a second guide portion which cooperates with the first guide portion is disposed on the body part, and the second guide portion is configured to move along the first guide portion, so as to move the liquid storage chamber into or out of the second accommodating part.

11. The immunoassay device of claim 1, further comprising: a chip clamp disposed in the first accommodating part and configured to clamp the detection chip.

12. The immunoassay device of claim 11, wherein the chip clamp comprises a first clamping portion and a second clamping portion hinged to each other; wherein, a second groove is disposed on a side of the first clamping portion facing the second clamping portion, the second groove is configured to accommodate the detection chip; the second clamping portion has a first open hole and a second open hole, the first sealing member is disposed in the first open hole, and a second sealing member is disposed in the second open hole, the first sealing member having a first through hole, and the second sealing member having a second through hole; the first through hole has a first bottom end opening close to the detection chip and a first top end opening away from the detection chip, the first top end opening communicating with the driving assembly; and the second through hole has a second bottom end opening close to the detection chip and a second top end opening away from the detection chip;

wherein, when the chip clamp is in a clamping state, the first sealing member and the second sealing member are both in close contact with the detection chip, an orthographic projection of the first bottom end opening of the first through hole on the detection chip overlaps with an area where the liquid inlet of the detection chip is located; and an orthographic projection of the second bottom end opening of the second through hole on the detection chip overlaps with an area where the liquid outlet of the detection chip is located.

13. The immunoassay device of claim 12, wherein, when the chip clamp is in the clamping state, the area where the liquid inlet of the detection chip is located is within an orthographic projection range of the first bottom end opening on the detection chip; the area where the liquid outlet of the detection chip is located is within an orthographic projection range of the second bottom end opening on the detection chip.

14. The immunoassay device of claim 12, wherein the first sealing member and the second sealing member are each an elastic member, and the first sealing member and the second sealing member are each in a compressed state when the chip clamp is in the clamping state.

15. The immunoassay device of claim 12, wherein the liquid storage chamber comprises: a first liquid tank and a second liquid tank, the first liquid tank is configured to store the reagent, a liquid outlet of the first liquid tank serves as the liquid outlet of the liquid storage chamber; and the second liquid tank is configured to store waste liquid discharged from the detection chip, a liquid inlet of the second liquid tank communicates with the second top end opening of the second through hole.

16. The immunoassay device of claim 12, wherein a connecting member is disposed at an end of the first clamping portion away from a hinged position; an engaging member is disposed at an end of the second clamping portion away from the hinged position, and when the chip clamp is in the clamping state, the connecting member is engaged with the engaging member.

17. The immunoassay device of claim 1, wherein the housing has a length between 25 cm and 40 cm, a width between 20 cm and 30 cm, and a height between 15 cm and 25 cm; and a dimension of the detection chip is between 70 mm and 80 mm in length, between 20 cm and 30 cm in width and between 1.0 mm and 2.0 mm in thickness.

18. An immunoassay method for an immunoassay device of claim 1, the immunoassay method comprising:

adding a sample solution with antigen into the detection chip to combine at least a part of the antigen in the sample solution with a fluorescent antibody preset in the detection chip, and a complex formed after combination is captured by a capture object preset in the detection chip;

and utilizing the driving assembly to drive the liquid outlet of the liquid storage chamber to communicate with the liquid inlet of the detection chip, and drive the reagent in the liquid storage chamber to enter the detection chip, so as to wash away the fluorescent antibody that is not combined with the antigen.

* * * * *